United States Patent [19]

Sato

[11] 4,213,462
[45] Jul. 22, 1980

[54] OPTICAL ASSEMBLY FOR DETECTING AN ABNORMALITY OF AN ORGAN OR TISSUE AND METHOD

[76] Inventor: Nobuhiro Sato, 5-11, 1-Chome, Tachibana-Cho, Toyoraka-shi, Osaka-fu, Japan

[21] Appl. No.: 934,681

[22] Filed: Aug. 18, 1978

[30] Foreign Application Priority Data

Aug. 25, 1977 [JP] Japan .................................. 52-102280

[51] Int. Cl.² .............................................. A61B 5/00
[52] U.S. Cl. .................................... 128/634; 356/434
[58] Field of Search ....................... 128/633, 634, 665; 356/39, 434, 435

[56] References Cited

U.S. PATENT DOCUMENTS

| | | | |
|---|---|---|---|
| 2,437,916 | 3/1948 | Greenwald | 128/665 |
| 2,790,438 | 4/1957 | Taplin et al. | 128/633 |
| 3,412,729 | 11/1968 | Smith, Jr. | 128/633 |
| 3,461,856 | 8/1969 | Polanyi | 128/633 |
| 3,811,777 | 5/1974 | Chance | 128/633 |
| 3,825,342 | 7/1974 | Lubbers et al. | 128/633 |

FOREIGN PATENT DOCUMENTS

2053301 5/1972 Fed. Rep. of Germany ............ 128/634
311618 10/1971 U.S.S.R. ................................... 128/665

OTHER PUBLICATIONS

Sakita et al., Image Technology and Information Display, Sep. 1975, pp. 55–58.

Primary Examiner—Lee S. Cohen
Attorney, Agent, or Firm—Jackson, Jones & Price

[57] ABSTRACT

The present invention relates to a method of detecting an abnormality of cell growth in an organ or tissue of a body and various optical assemblies for accomplishing the same. The present invention has discovered that diagnosis of incipient abnormal tissue growth such as cancer can be accomplished in vivo by exerting a predetermined pressure on the suspected tissue or organ and by subsequently comparing the relative effect on reflection from or light absorption of the tissue or organ. An optical probe can be utilized for scanning the suspected tissue or organ and recording an initial reflecting characteristic. Subsequently the tissue or organ is placed under a predetermined pressure to provide a second reflection characteristic. A comparison of the two signals will permit a diagnosis of the condition of the tissue or organ. As can be appreciated, a fiber optic bundle can be used for the optical probe and a data processor can automatically compute either the difference or the ratio of the two signals with a corresponding display or printing of the information. Alternative embodiments are disclosed herein.

21 Claims, 7 Drawing Figures

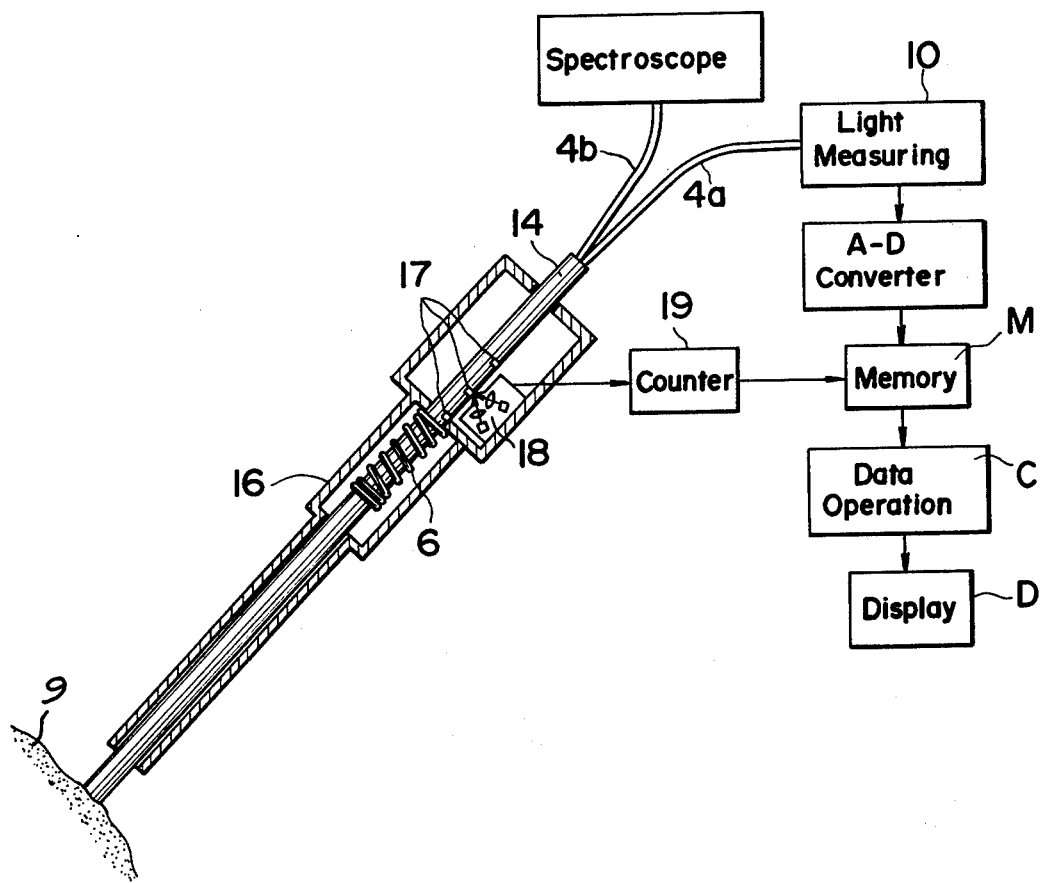

OPTICAL ASSEMBLY FOR DETECTING AN ABNORMALITY OF AN ORGAN OR TISSUE AND METHOD

BACKGROUND OF THE INVENTION

1. Field of the Invention

The present invention relates to a method and optical apparatus for detecting an abnormality of cell growth in an organ or tissue at an incipient stage by the measurement of light reflected from the organ or tissue in a normal condition and under a predetermined pressure.

2. Description of the Prior Art

Recent studies in the medical field have suggested that it is possible to detect an abnormality such as cancer in an organ or tissue of the human body by means of a spectral analysis of light directed to and reflected from an organ or a tissue. In this regard it has been discovered that the intensity of light reflected will vary across the visual spectrum of light and will generally decrease, at least between 500 and 600 nanometers depending upon the degree of cancer growth. Experiments in this area have been reported in a Japanese publication, Image Technology and Information Display, September, 1975 pages 55 to 58 by T. Sakita and H. Kumagai. In applying the suggested technique of this publication for the detection of cancer in an organ or a tissue of the human body, a bandwidth of light is directed to be reflected from the organ or tissue. During the measurement period, it is recommended that the end of the light guide optical fiber, which provides both the exit and entrance point for the light, should be in contact with the surface of the organ or the tissue for removing the influence of any surface mirror reflection of light from the organ or tissue to thereby eliminate any possible error readings.

Various attempts have been made in the prior art to permit an early detection of cancer at its incipient stage. As is well known in the medical profession, the sooner the cancerous growth is detected the greater the chance for successful preventative or curative medical treatment. When the cancer has reached an advance stage, it is relatively easy to determine by the color and light reflection and distinction between the cancerous tissue and that of the normal living portion. This has been more than adequately established by the above mentioned article. The detection, however, of cancer at its incipient state when it is proliferating in the normal organ or tissue, has proved more elusive to the efforts of the medical profession because an organ which is attacked by proliferating cancer with the cells still living can hardly be distinguished from a normal organ regardless of the degree or condition of the disease.

Accordingly, the medical profession is still seeking methods and apparatus that can be conveniently utilized in the monitoring of apparently healthy patients to provide an early diagnosis of cancer.

As can be generally appreciated, a large number of optical catheters and endoscopic instruments are known in the medical profession. The Richards U.S. Pat. No. 3,091,235 provides an illustrative example of such an instrument. U.S. Pat. No. 2,922,873; U.S. Pat. No. 2,932,294; U.S. Pat. No. 3,123,066; U.S. Pat. No. 3,470,876; U.S. Pat. No. 3,655,259 and U.S. Pat. No. 3,814,081 are cited of general interest to show other various forms of optical catheters and endoscopic instruments. The particular design characteristics of these instruments, other than the modifications to accomplish the purpose of the present invention and the method by which the embodiments of the present invention are utilized are not important for an understanding of the present invention since they are known in the prior art.

SUMMARY OF THE INVENTION

An object of the present invention is to provide an optical device and method for detecting at an early stage any abnormality, for example cancer in an organ or tissue.

Another object of the present invention is to provide an optical device capable of detecting an abnormality of an organ or tissue in vivo which cannot be detected by a conventional optical analysis, or by an observation of the shape and color of an organ or tissue through an optical fiber scope.

The present invention is characterized by the discovery that a pair of measurements of the reflection characteristics of light from the surface of an organ or tissue that is subject to a differential in pressure, can be utilized in the diagnosis of an incipient proliferating cancerous state. Basically, a measurement, for example, of the relative measure of light absorption of at least one and preferably a bandwith of wavelengths, is taken from the tissue or organ in vivo by an optical probe such as an endoscope. A predetermined pressure is then exerted and a subsequent measurement of the relative light absorption or intensity during or after pressurization is accomplished. A comparison between the two signals will be indicative of the condition of the tissue and is quite capable of serving as a diagnosis of an abnormality such as cancer at its early incipient stages.

Various apparatus such as rotatable prisms can be utilized to provide a spectral analysis and conventional data processing equipment such as micro processors can be utilized to compute and display in any desired format the results to assist in the diagnosis. Preferred forms of the present invention which are each believed to be unique in their own right, although within the generic principles of the present inventive discovery, are set forth in the following specification and drawings.

The features of the present invention which are believed to be novel can be best understood, together with further objects and advantages, by reference to the following description, taken in connection with the accompanying drawings.

BRIEF DESCRIPTION OF THE DRAWINGS

FIG. 6 represents still another embodiment of the present invention.

BRIEF DESCRIPTION OF THE PREFERRED EMBODIMENTS

The following description is provided to enable any person skilled in the medical and medical instrument field to make and use the invention and to practice the method of the present invention and sets forth the best modes contemplated by the inventor of carrying out his invention. Various modifications, however, will remain readily apparent to those skilled in this field, since the generic principles of the present invention have been defined herein specifically to provide an early disclosure of the invention to assist the medical profession.

The present invention is characterized by at least two measurements of the light absorption or reflectance characteristics from the surface of an organ or tissue in vivo. A substantial differential in pressure exerted on the organ or tissue between the two measurements is utilized in the diagnosis of an abnormality such as the early stages of cancerous growth. An important feature of the present invention is to provide a method and apparatus for detecting the amount of change in the two measurements as a result of the variation of pressure on the organ or tissue. It is contemplated that an optical probe such as an endoscope, catheter or tracheascope can be utilized to accomplish the examination of the cavities of a body and determine the condition of the organs or tissue. The basic structure of these optical instruments are well known in the medical profession and need not be included herein to provide an understanding of the present invention. Reference is simply made to the Richards U.S. Pat. No. 3,091,235 for background information, and it is incorporated herein by reference for that purpose.

An important contribution of the apparatus and method of the present invention is not only the early detection of the incipient cancerous growth but also the assistance it can provide in the surgical removal of that growth. In a conventional surgical operation to remove a cancerous growth, a seemingly normal portion surrounding the apparently abnormal portion is removed in an attempt to provide a margin of safety to be sure that the abnormal portion is isolated and sufficiently removed from the organ or tissue. It is believed that the utilization of the method and apparatus of the present invention may contribute to minimizing that portion of the tissue or organ which must be removed by providing an improved detection capability of determining the extent of the abnormality.

Figure 1A:
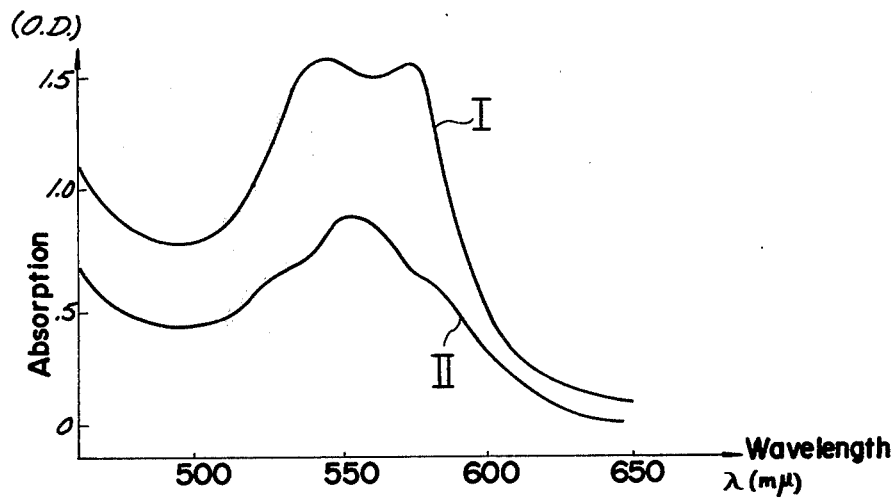
FIG. 1a discloses the wavelength characteristics of relative light absorption for a normal organ with and without pressure exerted thereon.

Referring to FIG. 1a, a spectral reflection curve of the experimental results on a human liver that represents healthy normal tissue is disclosed. Curve I discloses the measurement result from the liver with no substantial pressure exerted thereon. Curve II corresponds to the spectral reflection characteristic from the healthy liver tissue under a predetermined pressure. As can be determined from a comparison of these two curves in FIG. 1a, the reflection characteristic varies considerably with healthy tissue according to whether or not it is placed under pressure. The light absorption is reduced when the organ has been compressed and a characteristic whitening will occur.

Figure 1B:
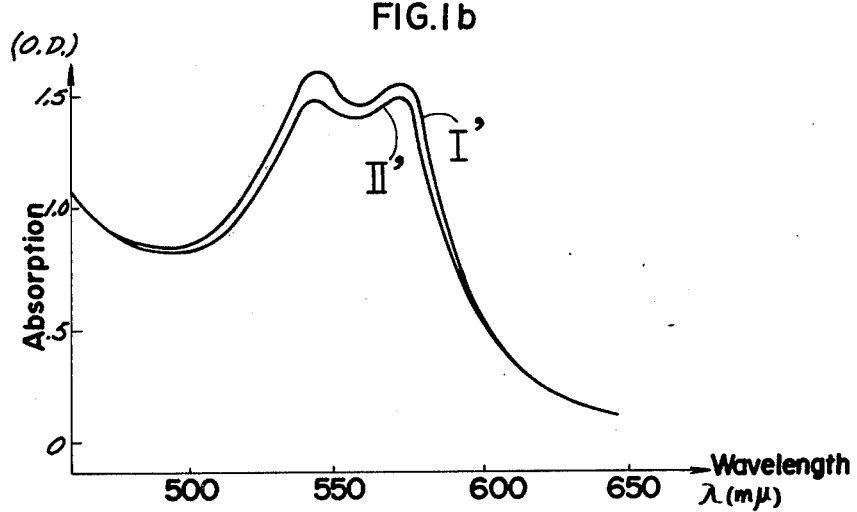
FIG. 1b discloses the wavelength characteristics of relative light absorption for an abnormal organ with and without pressure exerted thereon.

FIG. 1b discloses a spectral reflection characteristic of a human liver having a living cancerous growth that is proliferating in the organ. Again curve I' represents the output signal corresponding to the human liver being placed under substantially no pressure. Curve II' on the other hand, discloses the reflection characteristic signal with a predetermined pressure exerted on the organ. As can be readily seen in FIG. 1b, there is a relatively small difference in the reflection characteristics on the cancerous human liver with respect to the presence or absence of pressure.

It is believed that these readings result because the abnormal tissue may be so toughened or inflexible that the blood contained within this tissue will not be occulated by the pressure, and therefore there will not be any relative difference in the spectral reflection characteristic of the organ. Since the healthy soft tissue will permit the exclusion of the blood under pressure, there is a considerable change in the light absorption of the tissue as shown in FIG. 1a.

In both FIGS. 1a and 1b the absorption measurement is based on an O. D. scale, that is, optical density. Briefly optical density is simply a relatively measure of light absorption as compared to that of a standard reference target. For example, O. D. 1 refers to an intensity of light reflected from the tissue which is one tenth of that from a standard object, while O. D. 2 would correspond to the case of a reflective light intensity being one hundredth of that from a standard reference object.

The pressure exerted on the tissue or organ to provide the respective measurement curves II and II' in FIGS. 1a and 1b was approximately several hundred grams per square centimeter. With respect to the measurement curves I and I' the transparent end of the optical probe was only positioned in contact with the surface of the human liver and the pressure was considered to be substantially zero relative to that of the predetermined pressure exerted for the measurements of II and II'.

As a result of the present invention, it is now capable to measure cancer in the human liver while it was still living and proliferating at an early stage. In the crudest form of the present invention, it is capable to practice the method of the present invention by visually noting a relative variation of intensity of light upon an initial contact of the living tissue and the reflection of light with no pressure and a subsequent reflection of light from a pressurized tissue.

Referring again to FIG. 1a and FIG. 1b, it can be seen from the comparison of the curves I and I' that the reflection characteristics of the abnormal and healthy tissues are substantially identical when the optical probe is simply placed into contact with the tissue. Thus a measurement without a subsequent exertion of pressure would fail to provide a visual differentiation of abnormal tissue from the healthy tissue. This is particularly true in a precancerous tissue or incipient living cancerous growth condition of the tissue or organ.

Thus, the broadest application of the present invention provides a method of diagnosis of cancerous cell growth at an early stage by measuring the reflection of light from an organ or a tissue in vivo by a comparison of the resulting reflection signals with the subject tissue or organ monitored with and without a predetermined amount of pressure.

Figure 2:
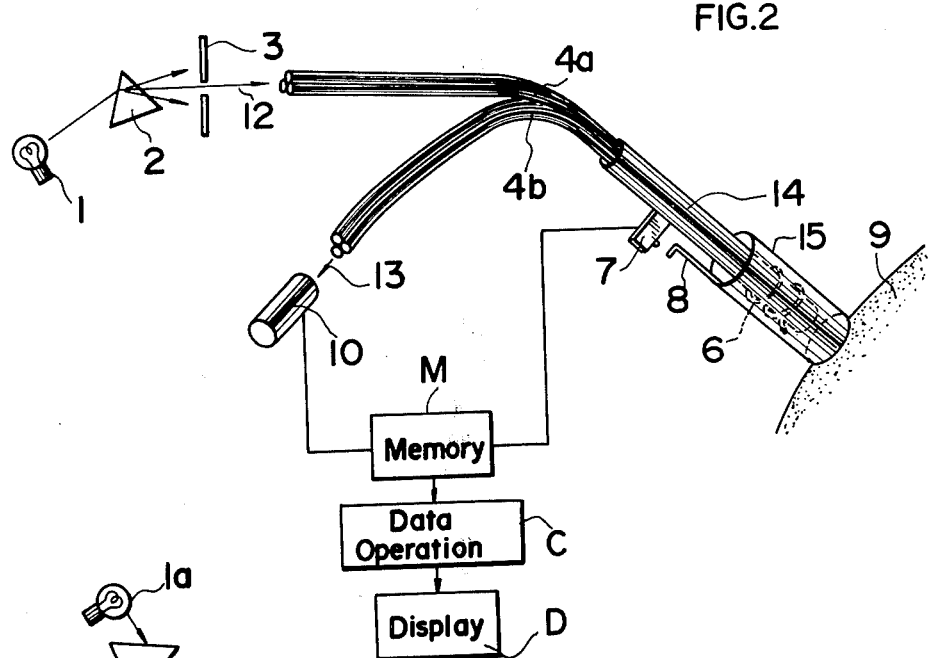
FIG. 2 represents a schematic illustration of a first embodiment of the present invention.

FIG. 2 discloses one form of apparatus for accomplishing the diagnosis method of the present invention. A light source 1 such as a tungsten-iodine lamp, xenon lamp or a mercury-vapor lamp is capable of emitting a spectrum of light rays of various wavelengths. A spectroscopic element 2 which, for purposes of illustration, can be shown as a prism, and a slit member 3 can be utilized to provide a variable wavelength source. A desired wavelength or wavelengths of light can thus be transmitted through the slit 3 to an optical fiber bundle 4a. The optical fiber bundle 4a can be of a conventional design and is capable of transmitting the light emerging from slit 3 into a human body. The optical fiber bundle 4b is capable of transporting the light reflected from the surface of an organ or tissue in vivo and under examination to a light receiving element 10. A conduit pipe 14 can provide a common housing for the respective optical fiber bundles 4a and 4b. The conduit pipe 14 can in turn, be slideably accommodated in a sheath or jacket 15. Mounted between the conduit pipe 14 and the jacket 15 is a spring 6 that is positioned so that spring energy or force can be generated as the conduit pipe 14 is pushed further into the jacket 15. The spring constant of the spring 6 is for example, a hundred grams per centimeter. The jacket 15 is provided at its furthest end, with a transparent bottom member or scanner or transparent material which is adapted to be held against the organ or tissue to be examined. The surface area of the bottom of jacket 15, which will be in contact with the organ or tissue, is 38.5 millimeters square. As can be appreciated, the jacket 15 may be entirely constructed of a suitable light transparent material rather than just having the bottom portion formed of the transparent material. A suitable transparent liquid can also be placed in the annular clearance between the conduit pipe 14 and the jacket 15.

The organ or tissue to be examined has been indicated in FIG. 2 as the subject matter 9. The optical probe is inserted against the organ 9 to be examined from the outside of the body, for example into the stomach through the esophagus and is subsequently brought into contact with the inside wall of the organ, e.g. the stomach. This can be accomplished in a known matter that need not be described in detail here. Initially the scanning bottom of the jacket 15 is held against the surface of the organ 9 without any substantial pressure. The wavelength of the incident light 12 is varied and a reflected light 13 from the surface of the organ is measured by the light receiving element 10. This measured information or data is stored in a memory bank M.

Subsequently, the conduit pipe 14 is moved relative to the jacket 15 thereby creating a spring force that will exert a pressure against the organ 9. To insure that a predetermined pressure will be applied to the organ 9, the conduit pipe 14 is provided with a switch mechanism 7 and the jacket member 15 has, secured thereto, a stopper member 8 so that the conduit pipe 14 can only be moved relatively into jacket 15 until the stopper 8 pushes the switch 7 and closes it. As can be readily understood, these elements have only been shown schematically to teach the principles of the present invention and quite obviously the actual physical envelope of the optical probe and the component parts would accommodate the intended usage. While switch 7 can be designed to be closed when the conduit pipe 14 sinks a relatively small distance into jacket 15, for example by about 20 millimeters, it can be readily understood that spring 6 can be so mounted that this movement will be sufficient to generate any predetermined pressure such as several hundred g/cm$^2$.

In the embodiment of FIG. 2, the wavelength of the incident light 12 can be altered when the switch 7 is closed and the reflected light 13 can be measured and stored in the memory M. The variation of wavelength can take place fast enough so that during the closing of switch 7 the pressure can be considered to be of a predetermined constant value. The spectral absorption data, which is fed to memory M, thereby corresponds to the condition of the tissue when it is initially placed under no pressure, and in its subsequent condition when it is placed under a predetermined pressure. These bits of information can then be processed by the data operational circuit C and the signal outputs of this circuit can then be displayed on any desired display medium D. The curves illustrated in FIGS. 1a and 1b are illustrative of such displays.

Since the principal data necessary for the utilization and diagnosis method of the present invention is the difference of the quantity of reflective light due to the presence or absence of a pressure, a data processor such as a micro processor can be programmed to compute the difference between the two data signals or the ratio of one to that of the other and the difference or ratio can then be computed and appropriately displayed. Since the important element in the diagnosis is the variation of the quantity of the reflective light due to the presence or absence of a pressure, the specific spectral characteristics of the entire optical assembly, and the spectral characteristics of the light source is not specifically critical to practice the present invention. Obviously however, a proper adjustment in calibration of the spectral characteristics of the light source and optics permits the optimization of the profiles of the absorption curves so that they can be utilized as diagnostic parameters in the same manner utilized in the conventional diagnostic procedures known in the medical profession.

Figure 3:
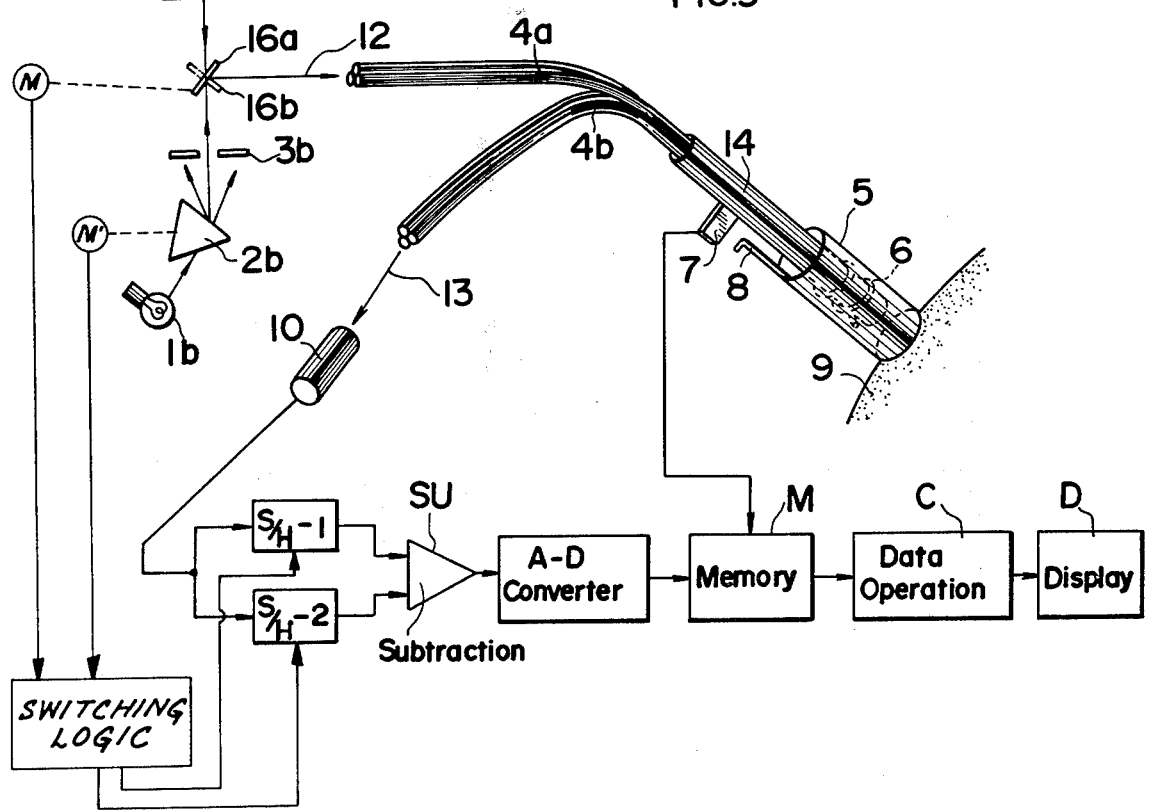
FIG. 3 represents a schematic illustration of a second embodiment of the present invention.

FIG. 3 discloses another embodiment of the present invention, wherein absorption characteristics are measured by at least two sets of light rays of two predetermined wavelengths. Elements 1a and 1b each denote a light source; 2a and 2b each denote a prism; and 3a and 3b refer to slits. Elements 2a and 3a as a group and 2b and 3b as a group, respectively, constitute independent spectroscopes. Emerging from the slits 3a and 3b are light rays of dissimilar wavelength. The light rays of these two different wavelengths are alternatingly made incident on an optical fiber bundle 4a by means of a mirror rotatable between positions 16a and 16b when driven by a known synchronous motor M. The construction and functions of the various parts, including the optical fiber bundles 4a and 4b, are the same as those described with reference to the embodiment of FIG. 2 and these like parts are designated by like reference numerals.

The sample light 13 emerging from optical fiber bundle 4b is photoelectrically transformed by a light-receiving element 10 and the output electrical signal is divided into signal components corresponding to the respective wavelengths by a known sequential timing relationship with the motor M that rotates mirrors and the motor M' which positions prism 2b. This relationship for coordinating the respective output signals from timing pulses is broadly described as switching logic in the schematic and is well known in the prior art as can be seen from U.S. Pat. No. 3,892,490 which is incorporated herein by reference for its general teaching of sampling and display features.

These individual signal components are then fed to sample and hold circuits S/H-1 and S/H-2, respectively, and a subtraction function is made by a known differential amplifier or subtraction circuit with SU. If the wavelength of the light emerging from slit 3b is varied by means of motor M' while the wavelength of emergent light from slit 3a is held constant by holding the prism 2a stationary to provide a reference level, the output of subtraction circuit unit SU is isolated from any noise effects of the spectral characteristics of optical fiber bundles 4a and 4b and the light-receiving element 10 by the known signal processing principle of a dual wavelength method so that the interchangeability of data obtained by individual apparatuses produced according to the present invention is enhanced.

As a result of the subtraction, the noise effect, which is assumed constant across the sampled wavelength spectrum is removed from the output envelope and the reference wavelength is the base line or reference level for the output envelope.

The output of subtraction circuit unit SU is converted from analog to digital information and stored in memory M and the two different sets of data according to the presence or absence of a pressure are displayed on a display D through a conventional data operation such as a microprocessor.

Figure 4:
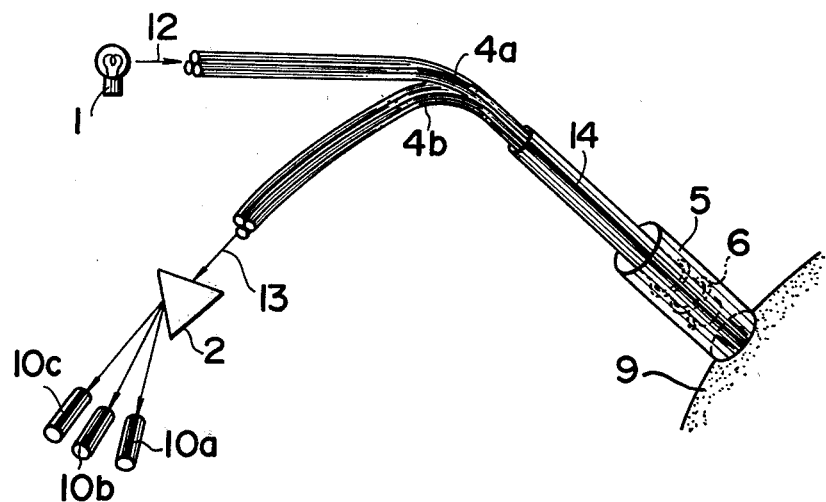
FIG. 4 discloses an alternative embodiment for directing and receiving light for use within the teachings of the present invention.

FIG. 4 shows another embodiment of the present invention. According to this embodiment, a multiwavelength of incident light is provided to the optical fiber bundle 4a, that is no spectroscopic setup is employed but, instead, the light from a light source 1 having a certain broad wavelength region is allowed to directly enter the optical fiber bundle 4a. The reflected light 13 is dispersed by a spectroscopic element 2 to obtain light rays of three (or any desired optical number) of dissimilar wavelengths which are respectively measured by light-receiving elements 10a, 10b and 10c. This arrangement can have an advantage of a reduced examination time when compared with a possible wavelength scanning procedure involving the use of a spectroscope described hereinbefore.

Figure 5:
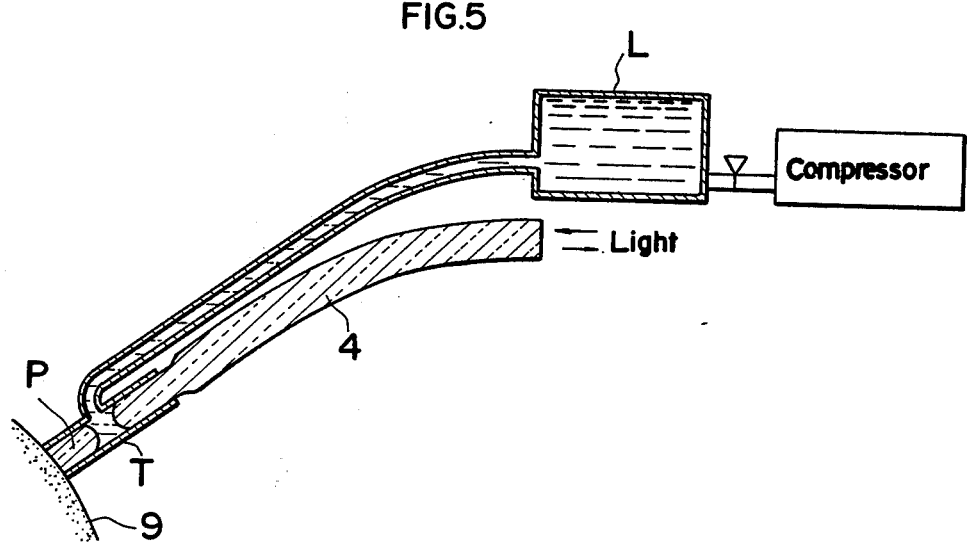
FIG. 5 discloses an alternative embodiment of exerting pressure on an organ or tissue in accordance with the teachings of the present invention.

FIG. 5 shows another example of a means for applying pressure to the organ or tissue under examination. A hollow cylinder T having smooth internal wall mates with a transparent piston P slideably installed therein. A light conductor 4 is attached to one end of the cylinder T and secured in a fluid tight relationship. The cylinder T has a branch portion which is in communication with a fluid reservoir L. As the fluid in the reservoir L is compressed, for example by a compressor as illustrated, the piston P is driven to pressure the tissue 9 to a predetermined level. The pressure thus applied to the tissue can be easily ascertained quantitatively from the fluid pressure within the fluid reservoir L and, therefore, can be accurately controlled.

FIG. 6 discloses still another arrangement for applying a predetermined pressure to the tissue. A conduit pipe 14 serving as a common housing for optical fiber bundles 4a and 4b has a transparent end which can be brought into direct contact with the tissue to be examined. A jacket 16 is fitted over the pipe 14, with a spring 6 being biased between jacket 16 and a collar formed on pipe 14. The mounting of the spring 6 is only schematically disclosed in FIG. 6. As the jacket 16 is pushed downward, the farthest end of pipe 14 progressively presses the tissue as a result of the spring force 6. The pipe 14 is marked, along a lateral side thereof, with a series of discrete signal marks 17 which may be successively scanned and detected by a photoelectric mark sensor 18 in response to the relative movement of the jacket 16 and pipe 14 as the jacket 16 is depressed. The detection signals are counted by a counter 19. This count represents the pressure applied to the organ or tissue which is being examined. The output of the counter 19 is stored in memory M and processed together with the output of the light measuring element 10 to compute the magnitude of difference in reflection characteristics of the tissue between two or more predetermined pressures. The analog to digital converter, data operation and display are all within known skill in the medical electronic field and need not be described herein.

It should be understood that in each of the above embodiments, the optical fiber bundles may be replaced with other conventional light conductors such as mere metal tubes with a feature of total internal reflection. It is also possible to employ filters in lieu of prisms. Furthermore, in the embodiment described with reference to FIG. 4, it is possible to employ a photo diode array, for example of 256 or 1024 bits, instead of the light-receiving elements 10a, 10b and 10c so as to instantly measure a virtually continuous wavelength distribution of reflected light. Thus, the invention in this case, would also be applicable to living tissues and organs whose reflections are time-dependent. Further, the use of white light source as in FIG. 4 has an advantage in that the measurement need not be practiced in a darkroom since the measurement is not disturbed even if any ambient light enters the optical fiber bundle 4a.

It is to be further understood that various modifications of the generic concepts of this invention are possible without departing from its spirit and accordingly the scope of the present invention should be determined solely from the following claims.

What is claimed is:

1. An optical device for detecting an abnormality in an organ or tissue in its early stages of growth comprising:
   a light source assembly;
   contact means including a portion for contacting a surface of an organ or tissue and capable of exerting a predetermined pressure thereon;
   first means for transmitting light from the light source assembly to the tissue or organ that will be effected by the predetermined pressure;
   means for measuring the light intensity reflected from the organ or tissue;
   second means for transmitting reflected light from the tissue or organ that will be effected by the predetermined pressure to the means for measuring the light intensity;
   means for determining a first measurement of light reflected from the organ or tissue with approximately no pressure applied and for determining a second measurement at a predetermined pressure, and
   means for comparing the first and second measurements to detect whether an abnormality exists in the organ or tissue as a function of the difference in measured reflected light.

2. The invention of claim 1 wherein the first and second means for transmitting light are optical fibers capable of entering a cavity of the human body.

3. The invention of claim 1 wherein the light source assembly includes a multi-wavelength light source and the means for measuring the light intensity includes a detector for measuring the intensity of different wavelengths.

4. The invention of claim 1 wherein the contact means includes a probe member capable of entering a cavity of the human body and means for exerting a predetermined pressure on the organ or tissue in correlation with the means for determining a first and second measurement of reflected light.

5. The invention of claim 4 further including a reference wavelength from the light source assembly and a circuit means for removing noise from the measurements as a function of the difference between the reference wavelength measurement and the first and second measurements.

6. An optical device for detecting an abnormality of an organ or tissue in its early stages of growth comprising:
 a first light source means of a predetermined light intensity;
 a second contact means including a transparent portion capable of contacting a surface of an organ or tissue and exerting a predetermined pressure thereon;
 third means for transmitting light from the first light source means to the transparent portion of the second contact means;
 fourth means for measuring reflected light from the organ or tissue to produce at least a pair of signals, a first signal representative of light reflected when substantially no pressure is exerted by the transparent portion and a second signal representative of light reflected when a predetermined pressure is exerted on the organ or tissue by the transparent portion including comparison means for providing a quantitative measurement of the two signals in such a format to permit subsequent comparison processing to determine the existence of an abnormality of an organ or tissue by a substantial similarity in detected reflected light energy;
 fifth means for transmitting the light reflected from the organ or tissue through the transparent portion to the fourth measuring means;
 sixth means for forcing the transparent portion against the surface of the organ or tissue at a predetermined pressure, and
 seventh means for detecting the predetermined pressure condition and correlating the resulting measurement by the fourth means.

7. The invention of claim 6 further comprising an eighth means for storing the first and second light measuring signals of the fourth means.

8. The invention of claim 7 further comprising a ninth means connected to the eighth means for deriving signals from the stored first and second light measuring signals according to a predetermined data operation function and a tenth means responsive to the signals of the ninth means for displaying the contents of the signals.

9. The invention of claim 8, wherein the first means includes a spectroscope and the fourth means includes a light measuring element.

10. The invention of claim 8, wherein the first means includes a device for emitting light across a wide band of wavelengths and the fourth means includes means for deriving a spectrum from the light transmitted by the fifth means and means for individually receiving a plurality of colors of light in the spectrum.

11. The invention of claim 6, wherein the second means includes a first member which is free from any contact with the organ or tissue and a second member having the transparent portion and being movable relatively to the first member.

12. The invention of claim 11 wherein the sixth means includes a spring connected between the first and second members.

13. The invention of claim 11, wherein the sixth means includes a fluid filled between the first and second members and means for varying the pressure of the fluid and wherein the seventh means further includes a device for detecting the pressure of the fluid.

14. The invention of claim 11, wherein the seventh means includes a device for detecting the position of the second member relative to the first member.

15. The invention of claim 14, wherein the detecting device is a switch which can be closed in accordance with a change in the position of the second member relative to the first member.

16. The invention of claim 14, wherein the detecting device includes an optical means for reading the position of the second member relative to the first member to derive an output pulse signal and a counter for counting the output pulse signal.

17. A method of optically detecting an abnormality such as cancer at its incipient stage of growth in a body portion of an organ or tissue in vivo comprising the steps of;
 directing a first quantity of light energy at the body portion under diagnoses of such a wavelength that it is reflectable from the surface of the organ or tissue;
 detecting the intensity of first light energy reflection from the body portion;
 placing the body portion under a predetermined pressure;
 directing a second quantity of light energy at the body portion under diagnoses;
 detecting the intensity of second light energy reflection from the body portion under diagnoses, and
 comparing the first and second detected light energy reflection whereby a substantial similarity in detected intensity of light energy reflection indicates an abnormal condition in the body portion.

18. The invention of claim 17 wherein a spring force is used to apply the predetermined pressure to the body portion.

19. The invention of claim 17 wherein a liquid pressure force is used to apply the predetermined pressure to the body portion.

20. The invention of claim 17 wherein the directing steps include directing a multi-wavelength of light energy in the visible spectrum at the body portion.

21. The invention of claim 20 further including directing at least a third wavelength of energy at the body portion to provide a reference for removing any error noise for the detected intensity.

* * * * *

UNITED STATES PATENT AND TRADEMARK OFFICE
CERTIFICATE OF CORRECTION

PATENT NO. : 4,213,462
DATED : July 22, 1980
INVENTOR(S) : Nobuhiro Sato

It is certified that error appears in the above—identified patent and that said Letters Patent is hereby corrected as shown below:

Column 2, line 66, delete "teachings" and insert --teaching--.

Column 9, line 30, delete "of" and insert --in--

Signed and Sealed this

Twenty-third Day of December 1980

[SEAL]

Attest:

SIDNEY A. DIAMOND

Attesting Officer　　　Commissioner of Patents and Trademark